(12) United States Patent
Dubief et al.

(10) Patent No.: US 6,368,606 B1
(45) Date of Patent: *Apr. 9, 2002

(54) COSMETIC COMPOSITION FOR THE TREATMENT OF KERATINOUS MATERIALS COMPRISING AT LEAST A GRAFTED SILICONE POLYMER AND AT LEAST AN AQUEOUS DISPERSION OF INSOLUBLE PARTICLES OF NON IONIC OR CATIONIC POLYMER

(75) Inventors: Claude Dubief, Le Chesnay; Christine Dupuis, Paris, both of (FR)

(73) Assignee: L'Oreal, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,793

(22) PCT Filed: Oct. 8, 1996

(86) PCT No.: PCT/FR96/01570

§ 371 Date: Sep. 2, 1998

§ 102(e) Date: Sep. 2, 1998

(87) PCT Pub. No.: WO97/14400

PCT Pub. Date: Apr. 24, 1997

(30) Foreign Application Priority Data

Oct. 18, 1995 (FR) .............................................. 95 12235

(51) Int. Cl.$^7$ ................................................. A61K 7/00
(52) U.S. Cl. ................... 424/401; 424/70.1; 424/70.12; 424/70.15; 424/70.16; 514/880; 514/881
(58) Field of Search ............................. 424/70.1, 70.12, 424/70.15, 70.16, 401; 514/880, 881

(56) References Cited

U.S. PATENT DOCUMENTS

| | | | |
|---|---|---|---|
| 4,673,568 A | * 6/1987 | Grollier et al. ................. 424/47 |
| 4,693,935 A | 9/1987 | Mazurek ....................... 428/352 |
| 4,728,571 A | 3/1988 | Clemens et al. .............. 428/352 |
| 4,972,037 A | 11/1990 | Garbe et al. .................. 526/245 |
| 5,166,276 A | 11/1992 | Hayama et al. ............. 525/329.7 |
| 5,441,728 A | 8/1995 | Tsaur et al. ................... 424/70.11 |
| 5,472,689 A | 12/1995 | Ito .............................. 424/70.122 |
| 5,480,634 A | 1/1996 | Hayama et al. ............... 424/70.12 |
| 5,567,428 A | 10/1996 | Hughes ........................... 424/401 |
| 5,637,306 A | * 6/1997 | Cauwet et al. ................. 424/401 |
| 5,709,850 A | * 1/1998 | Mondet et al. ............... 424/70.16 |

FOREIGN PATENT DOCUMENTS

| | | |
|---|---|---|
| EP | 0 388 582 | 9/1990 |
| EP | 0 408 311 | 1/1991 |
| EP | 0 412 704 | 2/1991 |
| EP | 0 412 707 | 2/1991 |
| EP | 0 524 612 | 1/1993 |
| EP | 0 582 152 | 2/1994 |
| FR | 2 697 160 | 4/1994 |
| FR | 2 709 955 | 3/1995 |
| WO | WO 93/03703 | 3/1993 |
| WO | WO 93/03704 | 3/1993 |
| WO | WO 93/23009 | 11/1993 |
| WO | WO 93/23446 | 11/1993 |
| WO | WO 95/00108 | 1/1995 |
| WO | WO 95/00578 | 1/1995 |
| WO | WO 95/03776 | 2/1995 |
| WO | WO-95/03776 A1 * | 2/1995 |
| WO | WO 95/05800 | 3/1995 |

OTHER PUBLICATIONS

English Language Derwent Abstract of FR 2 697 160. Apr. 29, 1994.
English Language Derwent Abstract of FR 2 709 955. Sep. 15, 1993.

* cited by examiner

Primary Examiner—Thurman K. Page
Assistant Examiner—Lakshmi Channavajjala
(74) Attorney, Agent, or Firm—Finnegan, Henderson, Farabow, Garrett & Dunner, LLP

(57) ABSTRACT

The present invention relates to a cosmetic or dermatological for the treatment of keratinous materials, particularly hair, comprising in a cosmetically or dermatologically acceptable medium at least a grafted silicone polymer with a polysiloxane skeleton grafted by organic non-silicone monomers and at least an aqueous dispersion of insoluble particles of nonionic or cationic polymer. The composition is particularly useful for rinsed products or as non rinsed products for washing hair, hair care, hair conditioning, hair dressing or hair setting.

39 Claims, No Drawings

COSMETIC COMPOSITION FOR THE TREATMENT OF KERATINOUS MATERIALS COMPRISING AT LEAST A GRAFTED SILICONE POLYMER AND AT LEAST AN AQUEOUS DISPERSION OF INSOLUBLE PARTICLES OF NON IONIC OR CATIONIC POLYMER

This application is a 371 of PCT/FR96/01570 filed Oct. 8, 1996.

The present invention relates to a cosmetic or dermatological composition for treating keratin substances, in particular the hair, comprising at least one grafted silicone polymer with a polysiloxane skeleton-grafted with non-silicone organic monomers, and at least one aqueous dispersion of insoluble particles of nonionic or cationic polymer.

It has been proposed to use aqueous dispersions of insoluble polymer particles in compositions for maintaining the hairstyle. However, the results obtained hitherto are still not satisfactory. The reason for this is that the fixing power is still not sufficient, the drying time is long and the cosmetic properties are still not satisfactory. Furthermore, the polymer is difficult to remove from the hair during washing with a shampoo.

Polymers with a polysiloxane skeleton grafted with non-silicone organic monomers are also known in the prior art. They are preferably chosen from those described in patent applications EP-A-0,582,152 and WO 93/23009. They are used in particular in hair compositions for their styling properties.

Compositions for washing and/or caring for and/or treating the hair containing styling polymers of this type in their formulation generally have the drawback of having a fixing power which is still insufficient.

The expression fixing power of the composition will be understood to denote the ability of this composition to give the hair cohesion such that the initial shape of the hairstyle is retained.

Compositions are thus still sought which do not have the drawbacks described above.

The Applicant has discovered, surprisingly, that by combining at least one silicone polymer having a polysiloxane skeleton grafted with non-silicone organic monomers with at least one dispersion of insoluble particles of nonionic or cationic polymer, the abovementioned drawbacks are overcome.

These compositions have good fixing power and good cosmetic properties such as disentangling and styling or brushing of the hair after application, the softness, the feel and the smoothness of the hair.

The composition according to the invention is thus essentially characterized in that it comprises, in a cosmetically or dermatologically acceptable medium, at least one grafted silicone polymer with a polysiloxane skeleton grafted with non-silicone organic monomers and at least one dispersion of insoluble particles of nonionic or cationic polymer.

In the following text, in accordance with what is generally accepted, the term silicone polymer is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bonding $\equiv$Si—O—Si$\equiv$), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy radicals or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

According to the present invention, the grafted silicone polymer(s) which is (are) to be used is (are) that (those) which comprise(s) a main silicone (or polysiloxane ($\equiv$Si—O—)$_n$) chain on which is grafted, inside the said chain as well as, optionally, on at least one of its ends, at least one organic group containing no silicone.

These silicone polymers can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv$Si—H groups and vinyl groups $CH_2$=CH—, or alternatively the reaction between thio functional groups —SH with these same vinyl groups.

Examples of silicone polymers which are suitable for carrying out the present invention, as well as their specific mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical (homo) polymerization of at least one anionic monomer of unsaturated carboxylic acid type can, after reaction, be post-neutralized with a base (sodium hydroxide, aqueous ammonia, etc) in order to bring it into the form of a salt.

According to the present invention, the hydrophobic monomers containing ethylenic unsaturation are preferably chosen, alone or as a mixture, from acrylic acid esters of alkanols and/or methacrylic acid esters-of -alkanols. The alkanols are preferably $C_1$–$C_{18}$ and more particularly $C_1$–$C_{12}$. The preferred monomers are chosen from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate, or mixtures thereof.

One family of grafted silicone polymers which is particularly suitable for carrying out the present invention consists of silicone polymers containing in their structure the unit of formula (I) below:

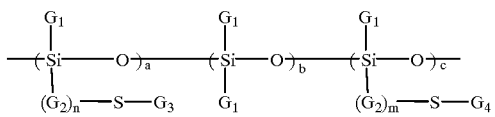

(I)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (I) above has at least one, and even more preferably all, of the following characteristics:

the radicals $G_1$ denote an alkyl radical, preferably the methyl radical;

n is non-zero and the radicals $G_2$ represent a divalent $C_1$–$C_3$ radical, preferably a propylene radical;

$G_3$ represents a polymeric radical resulting from the (homo)polymerization of at least one monomer of the carboxylic acid type containing ethylenic unsaturation, preferably acrylic acid and/or methacrylic acid;

$G_4$ represents a polymeric radical resulting from the (homo)polymerization of at least one monomer of the $C_1$–$C_{10}$ alkyl (meth)acrylate type, preferably of the isobutyl or methyl (meth)acrylate type.

Examples of silicone polymers corresponding to formula (I) are, in particular, polydimethylsiloxanes (PDMS) on which are grafted, via a thiopropylene-type connecting chain, mixed polymer units of the poly(meth)acrylic acid type and of the polymethyl (meth)acrylate type.

Other examples of silicone polymers corresponding to formula (I) are, in particular, polydimethylsiloxanes (PDMS) on which are grafted, via a thiopropylene-type connecting chain, polymer units of the polyisobutyl (meth) acrylate type.

Preferably, the number-average molecular mass of the silicone polymers of the invention, ranges approximately from 10,000 to 1,000,000 and even more preferably approximately from 10,000 to 100,000.

The grafted silicone polymers in accordance with the invention are preferably used in an amount ranging from 0.01 to 20% by weight relative to the total weight of the composition. More preferably, this amount ranges from 0.1 to 15% by weight and even more particularly from 0.5 to 10% by weight.

The aqueous dispersions of insoluble particles of nonionic or cationic polymer which can be used according to the invention are generally obtained by suspension or emulsion polymerization or copolymerization of monomers according to processes that are well known in the prior art (such dispersions are also known as "latices"). Aqueous polymer dispersions can also be obtained by dissolving the said polymer in a water-miscible organic solvent, after which water is added and lastly the organic solvent is evaporated off. This type of preparation is described, for example, in French patent application No. 2,697,160.

The average diameter of the insoluble polymer particles is generally less than 500 nm and preferably less than 250 nm. The glass transition temperature is generally between −30° C. and 90° C. and preferably between 10 and 35° C.

The polymer of the aqueous dispersion comprises at least one monomer chosen, for example, from styrene, butadiene, ethylene, tetrafluoroethylene, propylene, vinyltoluene, vinyl propionate, vinyl alcohol, acrylonitrile, chloroprene, vinyl chloride, vinyl acetate, urethanes, isoprene, isobutene and esters or amides of acrylic, methacrylic, maleic, crotonic or itaconic acid, vinyl ethers, vinylpyrrolidone, vinylimidazole, trimethylammonioethyl (meth)acrylate and mixtures thereof.

The aqueous dispersions which can be used according to the invention can come from the condensation of ionic or nonionic monomers giving nonionic or cationic polymers, such as, for example, polyesters, polyamides, polyurethanes or polyethers.

The nonionic polymers in the aqueous dispersions which can be used according to the present invention are chosen, for example, from the following compounds:

vinyl acetate homopolymers such as the product sold under the name Appretan EM by the company Hoechst or the product sold under the name Rhodopas A 012 by the company Rhône-Poulenc;

copolymers of vinyl acetate and of acrylic ester, such as the product sold under the name Rhodopas AD 310 by Rhône-Poulenc;

copolymers of vinyl acetate and of ethylene, such as the product sold under the name Appretan TV by the company Hoechst;

copolymers of vinyl acetate and of maleic ester, for example of dibutyl maleate, such as the product sold under the name Appretan MB Extra by the company Hoechst;

vinyl chloride homopolymers, such as the products sold under the names Geon 460X45, Geon 460X46 and Geon 577 by the company Goodrich;

polyethylene waxes, such as the products sold under the names Aquacer 513 and Aquacer 533 by the company Byk Cera;

polyethylene/polytetrafluoroethylene waxes, such as the products sold under the names Drewax D-3750 by the company Drew Ameroid and Wax Dispersion WD-1077 by the company R. T. Newey;

copolymers of polyethylene and of maleic anhydride;

alkyl acrylate homopolymers and alkyl methacrylate homopolymers, such as the product sold under the name Micropearl RQ 750 by the company Matsumoto or the product sold under the name Luhydran A 848 S by the company BASF;

copolymers of acrylic esters such as, for example, copolymers of alkyl acrylates and of alkyl methacrylates, such as the products sold by the company Rohm & Haas under the names Primal ACZ 61 k and Eudragit NE 30 D, by the company BASF under the names Acronal 601, Luhydraw LR 8833 or 8845, and by the company Hoechst under the names Appretan N 9213 or N9212;

copolymers of acrylonitrile and of a nonionic monomer chosen, for example, from butadiene and alkyl (meth) acrylates; mention may be made of the products sold under the names Nipol LX 531 B by the company Nippon Zeon or those sold under the name CJ 0601 B by the company Rohm & Haas;

styrene homopolymers such as the product Rhodopas 5051 sold by the company Rhône-Poulenc;

copolymers of styrene and of alkyl (meth)acrylate, such as the products Mowilith LDM 6911, Mowilith DM 611 and Mowilith LDM 6070 sold by the company Hoechst, the products Rhodopas SD 215 and Rhodopas DS 910 sold by the company Rhône-Poulenc and the product Uramul SC 70 sold by the company DSM;

copolymers of styrene, of alkyl methacrylate and of alkyl acrylate, such as the product Daitisol SPA sold by the company Wacker;

copolymers of styrene and of butadiene, such as the products Rhodopas SB 153 and Rhodopas SB 012 sold by the company Rhône-Poulenc;

copolymers of styrene, of butadiene and of vinylpyridine, such as the products Goodrite SB Vinylpyridine 2528X10 and Goodrite SB Vinylpyridine 2508 sold by the company Goodrich;

copolymers of styrene and of vinylpyrrolidone, such as the products Antara 450 and Cloud 285 sold by the company ISP;

polyurethanes, such as the products sold under the names Acrysol RM 1020 or Acrysol RM 2020 by the company Rohm & Haas and the products Uraflex XP 401 UZ and Uraflex XP 402 UZ by the company DSM Resins;

copolymers of alkyl acrylate and of urethane, such as the product 8538-33 from the company National Starch;

polyamides, such as the product Estapor LO 11 sold by the company Rhône-Poulenc.

The dispersions of insoluble particles of cationic polymer comprise, for example, the following polymers:

copolymers of acrylamide and of trimethylammonioethyl (meth)acrylate;

copolymers of alkyl methacrylate, of alkyl acrylate and of trimethylammonioethyl (meth)acrylate, such as the product Eudragit RL 30 D sold by the company Rohm Pharma.

The aqueous dispersions of insoluble polymer particles which are particularly preferred in the context of the invention are aqueous dispersions of insoluble particles of non-ionic polymer.

The weight concentration of the insoluble polymer particles in the compositions according to the invention is preferably between 0.1 and 50% by weight relative to the total weight of the composition, and preferably between 1 and 30%.

The cosmetically or dermatologically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and isopropanol, polyalcohols such as diethylene glycol, glycol ethers, glycol alkyl ethers or diethylene glycol alkyl ethers.

The grafted silicone polymers according to the invention can be dissolved in the said cosmetically acceptable medium or used in the form of an aqueous dispersion of insoluble particles.

The composition of the invention can also contain at least one additive chosen from thickeners, fatty acid esters, fatty acid esters of glycerol, volatile silicones, surfactants, fragrances, preserving agents, sunscreens, proteins, vitamins, polymers, plant, animal, mineral or synthetic oils or any other additive conventionally used in the cosmetics field.

These additives are present in the composition according to the invention in proportions which can range from 0 to 20% by weight relative to the total weight of the composition. The precise amount of each additive depends on its nature and is determined easily by those skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of a gel, a milk, a cream, a relatively thickened lotion or a mousse.

The compositions of the invention are used as rinse-out products or as leave-in products in particular to wash, care for, condition, maintain the style of or shape keratin substances such as the hair.

These compositions are more particularly styling products such as hairsetting lotions, blow-drying lotions, fixing compositions (lacquers) and styling compositions. The lotions can be packaged in various forms, in particular in vaporizers, pump-dispenser bottles or in aerosol containers in order to ensure application of the composition in vaporized form or in the form of a mousse. Such packaging forms are indicated, for example, when it is desired to obtain a spray, a lacquer or a mousse for fixing or treating the hair.

The compositions can also be shampoos, rinse-out or leave-in compositions, to be applied before or after shampooing, dyeing, bleaching, permanent-waving or straightening the hair.

When the composition according to the invention is packaged in aerosol form in order to obtain a lacquer or an aerosol mousse, it comprises at least one propellant which can be chosen from volatile hydrocarbons such as n-butane, propane, isobutane, pentane, a chloro and/or fluoro hydrocarbon, and mixtures thereof. Carbon dioxide, nitrous oxide, dimethyl ether, nitrogen or air, which is compressed, and mixtures thereof, can also be used as propellant.

Another subject of the invention is a process for treating keratin substances such as the hair, which consists in applying a composition as defined above to the hair and then optionally in rinsing with water.

The invention will now be illustrated more fully with the aid of the examples which follow, which should not be considered as limiting it to the embodiments described. In the text which follows, AM means active material.

EXAMPLE 1

Styling Aerosol Spray

| | |
|---|---|
| Grafted silicone polymer of formula (I) of polymethyl/methylsiloxane structure containing 3-propylthio polymethacrylic acid groups and 3-propylthio polymethyl methacrylate groups | 3 g |
| Vinyl acetate homopolymer as an aqueous dispersion containing 50% AM, sold under the name Appretan EM by the company Hoechst | 4 g AM |
| Aminomethylpropanol, qs 100% neutralization of the grafted silicone polymer | 30 g |
| Dimethyl ether | 30 g |
| Water qs | 100 g |

The composition is pressurized as an aerosol.

This composition was applied to dried hair, the hair then having a good feel, good maintenance and good hold over time.

The composition is easily removed on shampooing.

EXAMPLE 2

Styling Aerosol Spray

| | |
|---|---|
| Grafted silicone polymer of formula (I) of polymethyl/methylsiloxane structure containing 3-propylthio polymethacrylic acid groups and 3-propylthio polymethyl methacrylate groups | 4 g |
| Copolymer of styrene and of butadiene as an aqueous dispersion containing 50% AM, sold under the name Rhodopas SB 012 by the company Rhône-Poulenc | 2 g AM |
| Aminomethylpropanol, qs 100% neutralization of the grafted silicone polymer | |
| Dimethyl ether | 30 g |
| Water qs | 100 g |

The composition is pressurized as an aerosol.

This composition was applied to dried hair, the hair then having a good feel, good maintenance and good hold over time.

The composition is easily removed on shampooing.

What is claimed is:

1. A cosmetic or dermatological composition comprising, in a cosmetically or dermatologically acceptable medium, at least one grafted silicone polymer with a polysiloxane skeleton grafted with non-silicone organic monomers and at least one aqueous dispersion of insoluble particles of non-ionic or polymer.

2. A cosmetic or dermatological composition according to claim 1, wherein said at least one grafted silicone polymer and said at least one aqueous dispersion are present in said composition in a combined amount effective for treating a keratin substance.

3. A cosmetic or dermatological composition according to claim 1, wherein said at least one grafted silicone polymer comprises a main polysiloxane chain on which is grafted, inside said chain and optionally on at least one of its ends, at least one organic group containing no silicone.

4. A cosmetic or dermatological composition according to claim 1, wherein said at least one grafted silicone polymer is obtained by radical copolymerization of:

at least one non-silicone anionic organic monomer having ethylenic unsaturation and/or a non-silicone hydrophobic organic monomer having ethylenic unsaturation, and, at least one polysiloxane having in its chain at least one functional group capable of reacting with said ethylenic unsaturations of said non-silicone monomers.

5. A cosmetic or dermatological composition according to claim 4, wherein said at least one polysiloxane has more than one functional group in its chain.

6. A cosmetic or dermatological composition according to claim 4, wherein said non-silicone anionic organic monomer is selected from linear and branched unsaturated carboxylic acids.

7. A cosmetic or dermatological composition according to claim 6, wherein said non-silicone anionic organic monomer is selected from acrylic acid, methacrylic acid, maleic acid, maleic anhydride, itaconic acid, fumaric acid and crotonic acid and alkali metal, alkaline-earth metal and ammonium salts thereof.

8. A cosmetic or dermatological composition according to claim 4, wherein said non-silicone hydrophobic organic monomer is selected from acrylic acid esters of an alkanol and methacrylic acid esters of an alkanol.

9. A cosmetic or dermatological composition according to claim 8, wherein said alkanol is $C_1$–$C_{18}$.

10. A cosmetic or dermatological composition according to claim 8, wherein said non-silicone hydrophobic organic monomer is selected from isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate.

11. A cosmetic or dermatological composition according to claim 1, wherein said at least one grafted silicone polymer comprises, on the main silicone chain, at least one organic group of anionic nature obtained by radical (homo) polymerization of at least one anionic unsaturated carboxylic acid monomer, partially or totally neutralized in the form of a salt.

12. A cosmetic or dermatological composition according to claim 1, wherein said at least one grafted silicone polymer is selected from silicone polymers containing at least one unit of formula (I):

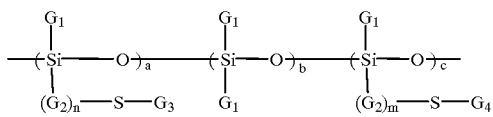

in which:

$G_1$ independently represent hydrogen or a $C_1$–$C_{10}$ alkyl radical or alternatively a phenyl radical;

$G_2$ independently represent a $C_1$–$C_{10}$ alkylene group;

$G_3$ represents a polymer residue from the (homo) polymerization of at least one anionic monomer containing ethylenic unsaturation;

$G_4$ represents a polymer residue from the (homo) polymerization of at least one hydrophobic monomer containing ethylenic unsaturation;

m and n are equal to 0 or 1;

a is an integer ranging from 0 to 50;

b is an integer ranging from 10 to 350; and c is an integer ranging from 0 to 50;

wherein either a or c is not 0.

13. A cosmetic or dermatological composition according to claim 12, wherein said unit of formula (I) has at least one of the following characteristics:

$G_1$ independently denote a $C_1$–$C_{10}$ alkyl radical;

n is not zero;

$G_2$ independently represent a divalent $C_1$–$C_3$ radical; and $G_3$ represents a polymeric radical from the (homo) polymerization of at least one carboxylic acid monomer containing ethylenic unsaturation; and $G_4$ represents a polymeric radical from the (homo) polymerization of at least one $C_1$–$C_{10}$ alkyl (meth) acrylate monomer.

14. A cosmetic or dermatological composition according to claim 12, wherein said unit of formula (I) simultaneously has the following characteristics:

$G_1$ denote a methyl radical;

n is not zero;

$G_2$ represent a propylene radical;

$G_3$ represents a polymeric radical from the (homo) polymerization of at least acrylic acid and/or methacrylic acid; and $G_4$ represents a polymeric radical from the (homo) polymerization of at least methyl (meth)acrylate.

15. A cosmetic or dermatological composition according to claim 1, wherein said at least one grafted silicone polymer has a number-average molecular mass ranging from 10,000 to 1,000,000.

16. A cosmetic or dermatological composition according to claim 15, wherein said at least one grafted silicone polymer has a number-average molecular mass ranging from 10,000 to 100,000.

17. A cosmetic or dermatological composition according to claim 1, wherein said at least one grafted silicone polymer is present in an amount ranging from 0.01 to 20% by weight relative to the total weight of said composition.

18. A cosmetic or dermatological composition according to claim 17, wherein said at least one grafted silicone polymer is present in an amount ranging from 0.1 to 15% by weight relative to the total weight of said composition.

19. A cosmetic or dermatological composition according to claim 18, wherein said at least one grafted silicone polymer is present in an amount ranging from 0.5 to 10% by weight relative to the total weight of said composition.

20. A cosmetic or dermatological composition according to claim 1, wherein the polymer of said at least one aqueous dispersion is formed from at least one monomer selected from styrene, butadiene, ethylene, propylene, vinyltoluene, vinyl propionate, vinyl alcohol, acrylonitrile, chloroprene, vinyl acetate, urethanes, isoprene, isobutene and esters and amides of acrylic, methacrylic, maleic, crotonic and itaconic acids, vinyl ether, vinylpyrrolidone, vinylimidazole, and trimethylammonioethyl (meth)acrylate.

21. A cosmetic or dermatological composition according to claim 1, wherein said nonionic polymer is selected from polyesters, polyamides, polyurethanes and polyethers.

22. A cosmetic or dermatological composition according to claim 1, wherein said nonionic polymer is selected from:

vinyl acetate homopolymers;

copolymers of vinyl acetate and of acrylic ester;

copolymers of vinyl acetate and of ethylene;

copolymers of vinyl acetate and of maleic ester;

vinyl chloride homopolymers;

polyethylene waxes;

polyethylene/polytetrafluoroethylene waxes;

copolymers of polyethylene and of maleic anhydride;

alkyl acrylate homopolymers and alkyl methacrylate homopolymers;

copolymers of acrylic esters;

copolymers of acrylonitrile and of a nonionic monomer;

styrene homopolymers;

copolymers of styrene and of alkyl (meth)acrylate;

copolymers of styrene, of alkyl methacrylate and of alkyl acrylate;

copolymers of styrene and of butadiene;

copolymers of styrene, of butadiene and of vinylpyridine;

copolymers of styrene and of vinylpyrrolidone; and copolymers of alkyl acrylate and of urethane.

23. A cosmetic or dermatological composition according to claim 22, wherein said copolymers of acrylic esters are selected from copolymers of alkyl acrylates and of alkyl methacrylates; or said copolymers of acrylonitrile and of a nonionic monomer are selected from butadiene and alkyl (meth) acrylates, or said copolymers of acrylic esters are selected from copolymers of alkyl acrylates and of alkyl methacrylates and said copolymers of acrylonitrile and of a nonionic monomer are selected from butadiene and alkyl (meth)acrylates.

24. A cosmetic or dermatological composition according to claim 1, wherein said insoluble polymer particles are present in an amount ranging from 0.1 to 50% relative to the total weight of said composition.

25. A cosmetic or dermatological composition according to claim 24, wherein said insoluble polymer particles are present in an amount ranging from 1 to 30% relative to the total weight of said composition.

26. A cosmetic or dermatological composition according to claim 1, further comprising at least one additive.

27. A cosmetic or dermatological composition according to claim 26, wherein said at least one additive is selected from thickeners, fatty acid esters, fatty acid esters of glycerol, silicones, surfactants, fragrances, preserving agents, sunscreens, proteins, vitamins, polymers, plant, animal, mineral and synthetic oils and any other additive conventionally used in the cosmetics field.

28. A cosmetic or dermatological composition according to claim 1, wherein said cosmetically or dermatologically acceptable medium comprises water or a mixture of water and at least one cosmetically acceptable solvent.

29. A cosmetic or dermatological composition according to claim 28, wherein said at least one cosmetically acceptable solvent is selected from monoalcohols, polyalcohols, glycol ethers, and fatty acid esters.

30. A cosmetic or dermatological composition according to claim 2, wherein said keratin substance is human hair.

31. A cosmetic or dermatological composition according to claim 1, wherein said composition is in the form of a gel, a milk, a cream, a lotion or a mousse.

32. A cosmetic or dermatological composition according to claim 1, wherein said composition is in the form of a styling product.

33. A cosmetic or dermatological composition according to claim 32, wherein said styling product is a hairsetting lotion, blowdrying lotion, hair fixing composition or hair styling composition.

34. A cosmetic or dermatological composition according to claim 1, wherein said composition is in the form of a shampoo or a rinse-out or leave-in hair product to be applied before or after shampooing, dyeing, bleaching, permanent-waving or straightening the hair.

35. A cosmetic or dermatological composition according to claim 1, wherein said composition is packaged in the form of a vaporizer, a pump-dispenser bottle or in an aerosol container.

36. A cosmetic or dermatological composition according to claim 1, wherein said at least one grafted silicone polymer is dissolved in the cosmetically or dermatologically acceptable medium or is in the form of an aqueous dispersion of insoluble particles.

37. A non-therapeutic process for treating a keratin substance comprising:

applying to said keratin substance a composition comprising, in a cosmetically or dermatologically acceptable medium, at least one grafted silicone polymer with a polysiloxane skeleton grafted with non-silicone organic monomers and at least one aqueous dispersion of insoluble particles of nonionic or polymer; and optionally rinsing with water.

38. A non-therapeutic process according to claim 36, wherein said keratin substance is hair.

39. A cosmetic or dermatological composition according to claim 35, wherein said composition is obtained from said aerosol container in the form of a spray, a laquer or a mousse.

* * * * *

UNITED STATES PATENT AND TRADEMARK OFFICE
CERTIFICATE OF CORRECTION

PATENT NO. : 6,368,606 B1
DATED : April 9, 2002
INVENTOR(S) : Claude Dubief et al.

It is certified that error appears in the above-identified patent and that said Letters Patent is hereby corrected as shown below:

<u>Column 7,</u>
Line 50, before "polymer" delete "or".

Signed and Sealed this

Ninth Day of July, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO. : 6,368,606 B1
DATED : April 9, 2002
INVENTOR(S) : Claude Dubief et al.

It is certified that error appears in the above-identified patent and that said Letters Patent is hereby corrected as shown below:

<u>Column 12,</u>
Line 3, after "nonionic" delete "or".

Signed and Sealed this

Twenty-second Day of October, 2002

Attest:

Attesting Officer

JAMES E. ROGAN
*Director of the United States Patent and Trademark Office*